United States Patent [19]
Frydrych

[11] Patent Number: 5,636,546
[45] Date of Patent: Jun. 10, 1997

[54] METHOD AND INSTALLATION FOR EVALUATING THE STICKING CHARACTER OF FIBROUS PLANT MATERIALS SUCH AS COTTONS

[75] Inventor: Richard Frydrych, Montpellier, France

[73] Assignee: Centre International de Recherche Agronomique pour le Developpement (C.I.R.A.D.), Montpellier, France

[21] Appl. No.: 232,039

[22] PCT Filed: May 11, 1993

[86] PCT No.: PCT/FR93/00457

§ 371 Date: Apr. 26, 1994

§ 102(e) Date: Apr. 26, 1994

[87] PCT Pub. No.: WO93/23752

PCT Pub. Date: Nov. 25, 1993

[30] Foreign Application Priority Data

May 20, 1992 [FR] France .................. 92 06142

[51] Int. Cl.⁶ .................. G01N 25/00; D06H 3/08
[52] U.S. Cl. .................. 73/159; 374/51
[58] Field of Search .................. 73/159; 374/51

[56] References Cited

U.S. PATENT DOCUMENTS

| | | | |
|---|---|---|---|
| 3,451,756 | 6/1969 | Young | 356/237 |
| 4,624,915 | 11/1986 | Schindler | 435/4 |
| 4,839,943 | 6/1989 | Leifeld | 19/80 R |
| 4,896,400 | 1/1990 | Polli | 19/27 |
| 5,003,670 | 4/1991 | Waeber et al. | 19/66 CC |
| 5,048,156 | 9/1991 | Waeber et al. | 19/66 CC |
| 5,130,559 | 7/1992 | Leifeld et al. | 250/562 |

FOREIGN PATENT DOCUMENTS

| | | |
|---|---|---|
| 2609058 | 7/1988 | France . |
| 3928279 | 2/1991 | Germany . |
| 4018847 | 12/1991 | Germany . |
| 50753 | 3/1988 | Japan . |
| 1193560 | 11/1985 | U.S.S.R. ............ 73/159 |

OTHER PUBLICATIONS

"Operating Instructions for SCT Honey–dew Testing Device GRAF/IRCT" Feb. 1992, Graf & Co. Ltd. Card Clothing and Machinery Manufactures.

Frydrych, R., "Determination du potentiel de collage des cotons par thermodetection", Cot. Fib.Trop., 1986, vol. XLI, fasc. 3.

Frydrych, Richard, "LA Thermodetection", Academie De Montpellier, Apr. 29, 1987, pp. 37–40, 49, 53–62.

*Primary Examiner*—William A. Cuchlinski, Jr.
*Assistant Examiner*—Willie Morris Worth
*Attorney, Agent, or Firm*—Rothwell, Figg, Ernst & Kurz, P.C.

[57] ABSTRACT

A sample of fibrous material prepared so that is has a large surface area relative to its weight. The sample is placed on a metal plate and then heated under pressure and successively cooled under pressure. A brush or sweeper then removes substantially all of the fibers left in the sample. If necessary, the sample is dried. The sample now consists of spots on the metal plate. An automatic counting system is used to count the number of spots to determine the sticky characteristic of the fibrous material.

23 Claims, 1 Drawing Sheet

METHOD AND INSTALLATION FOR EVALUATING THE STICKING CHARACTER OF FIBROUS PLANT MATERIALS SUCH AS COTTONS

FIELD OF THE INVENTION

The object of the invention is a method and an installation for the evaluation of the sticking character of fibrous plant materials such as cottons; the invention is also aimed at the use of this method and of this installation for carrying out, under the best conditions, successive operations in the treatment of fibrous materials contaminated in this way.

DESCRIPTION OF RELEVANT ART

For some years, fibrous plant materials, and particularly cottons of various origins, have produced a sticking effect during spinning, which has led to considerable losses of productivity.

The sticking is principally related to insect secretions known as "honey-dews", consisting mainly of sugar and giving cotton a sticking power.

In order to solve this problem, several methods have been proposed to determine and eliminate the honey-dews or their sticking action.

In particular, the applicant has designed a machine which, by examining a sample held at a precise hygrometric state and pressed between two suitably heated aluminium sheets, makes it possible to determine the sticking potential of the sample under examination.

This machine has the disadvantage that the procedure is relatively tricky to implement, takes a long time, is expensive and that, in addition, determination of the degree of sticking of the sample is still in the end very subjective and can vary considerably from one operator to another.

The object of the invention is to overcome these difficulties by allowing an accurate, rapid and economic evaluation of the sticking character of the fibrous material particularly through an improvement in the method and the machine that has just been described.

The method in accordance with the invention is characterised by the following successive steps:

- a sample of the fibrous material is prepared in such a way that it presents a large surface area in relation to its weight,
- the sample spread out in this way is applied to an aluminium or similar plate for several seconds using a pressing and heating unit,
- a cold pressure is then applied to the same sample on the same plate for several seconds,
- if necessary, a superficial drying of the plate is carried out with hot air,
- the fibres of the sample adhering to the plate are removed,
- the number of honey-dew spots adhering to the plate is counted, this number determining the sticking character of the sample brought to its spread-out area.

With advantage, a start is made from a sample of several grammes, for example with a weight of between 2 and 5 grammes, which is opened out over an area of several hundred cm², for example of the order of 200 cm². When proceeding in this way, it is observed that, all other things being equal, the number of honey-dew spots counted is independent of the weight of the sample, which therefore need not be accurately weighed, whereas it is easy to open it out over a given area, for example of 17×12 cm or about 200 cm².

With advantage, the heating is carried out at a temperature of between 33° and 140° C., preferably between 50° and 90° C.

The hot pressure may be maintained for several seconds and will be of the order of at least 40 g/cm², very satisfactory results being obtained with a pressure of between 80 g/cm² and 500 g/cm².

The lower the temperature, the higher the pressure and the longer this pressure will be maintained.

For example, excellent results are obtained with the following parameters:

a) temperature: 53° C., pressure: 500 g/cm², time for which the pressure is maintained: 30 seconds, b) temperature: 85° C., pressure: 80 g/cm², time for which the pressure is maintained: 5 seconds.

The cold pressure may be maintained for about 15 to 30 seconds, the pressure being of the same order of magnitude as that used for the hot pressure.

The method of the invention thus makes it possible in a very short space of time, less than 2 minutes, to determine accurately the sticking character of a cotton contaminated by honey-dews; an almost instantaneous knowledge of the sticking power of the cotton then makes it possible to determine without delay, and immediately to adapt, the treatment operations which are most appropriate for this cotton.

In particular, it is possible from a knowledge of this sticking power of the cotton to control an installation for a decontamination treatment of the same cotton.

In the same way, it is possible, from a knowledge of the sticking power of the cotton, to determine what type of spinning might possibly be implemented without a major disadvantage.

The invention is also aimed at installations permitting the automation or semi-automation of the method, as will result more clearly from the description which will follow, given with reference to the appended drawings in which:

DETAILED DESCRIPTION OF PREFERRED EMBODIMENTS

Figure 1:
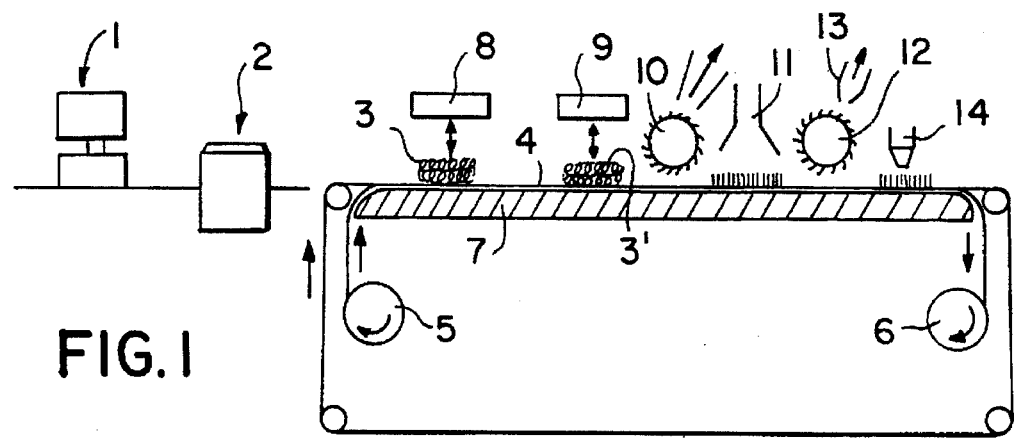
FIG. 1 shows schematically an installation for the implementation of the method of the invention according to a first embodiment.

Referring firstly to FIG. 1, the reference number 1 indicates a system for identifying samples, corresponding for example to determined bales of cotton, the said samples possibly being identified by a system using a bar-code reader, for example.

The reference number 2 indicates a diagrammatic representation of a system for preparing the sample, for example of the rotor type, making it possible to open out a sample of cotton which may weigh between 1 and 5 grammes, and generally between 2 and 3 grammes and which, once opened out, will occupy an area of about 17×12 centimeters (of the order of 200 cm²).

The sample is then placed, as indicated at 3, on a metal belt, with advantage made of aluminium 4, unwinding from a feed roller 5 and winding at the output of the machine on a take-up roller 6.

The sheet 4 advances above a neutral support 7, made for example of plastic or wood.

A heating plate 8 is heated to the chosen temperature between 33° C. and 140° C., preferably between 50° C. and 90° C.

When the sample 3 is in place under the heating plate 8, the latter is lowered in a controlled way and presses the sample against the aluminium sheet 4.

The pressure is maintained for a time which depends on the chosen temperature and which may be of the order of 5 to 30 seconds for example, for temperatures of the order of 85° C. to 53° C.

With advantage, the pressure lies between 40 g/cm² and 1000 g/cm², entirely satisfactory results being obtained with a pressure of between 80 g/cm² and 500 g/cm², higher pressures being used with advantage in conjunction with lower temperatures.

The combined action of pressure and heat exerted on the sample 3 causes a part of the moisture contained in the cotton to evaporate, creating a fine layer of water vapour over the aluminium support and making it possible at this level to soften the balls of sugar or honey-dews contained in the cotton, which then become attached to the aluminium support 4. In this connection, it should be pointed out that the action indicated assumes the existence of a certain moisture content in the cotton; in this case, a moisture content of the sample lying between 40% and 85% enables the required result to be obtained without difficulty, the measurement being in practice generally made for a moisture content close to 60–65%. It should be noted that it is the combined effect of a certain sample thickness, neither too small nor too great, and of the passage of the water vapour through the thickness of the sample which appears to make the measurement of the sticking character of the cotton independent of the tested weight of the sample.

When the hot pressing is finished, for example after 5 seconds, the plate 8 is raised, the belt 4 is advanced by one step and becomes located under the plate 9, which is then lowered and which will provide a cold pressure for the sample 3 which has moved to 3'.

The cold pressure may be maintained for about 15 to 30 seconds; its object is to ensure that the sticking spots are attached more firmly to the aluminium support 4.

The pressure of the cold plate 9 is with advantage of the same order of magnitude as that exerted by the heating plate 8.

At the end of this operation, the plate 9 is raised and a brush or sweeper 10 placed after the station 9 removes the majority of the fibres from the sample 3' when the belt 4 is advanced by one step as far as the station denoted by 11, which is a drying station.

At this point, the sample, if necessary, is dried by hot air so as to remove the residual moisture and to fix properly to the aluminium sheet 4 the sugar and honey-dew spots which are deposited on it. It has been observed that, in general, drying is not required if a relatively low hot-pressure temperature, typically between 50° C. and 55° C., and a sufficiently long maintenance of pressure, typically of the order of 30 seconds, are used.

The sample is then advanced to a brush 12, possibly coupled with a suction cleaning system 13, which removes the remaining fibres adhering to the plate.

At 14, it only remains to read, for example using a suitable camera, the number of spots left by the sample on the sheet 4.

This number of spots, brought to the surface of the prepared sample, makes it possible to determine accurately and automatically the sticking power or sticking quality of the cotton thus treated.

Of course, many variations may be made to the embodiment described.

Figure 2:
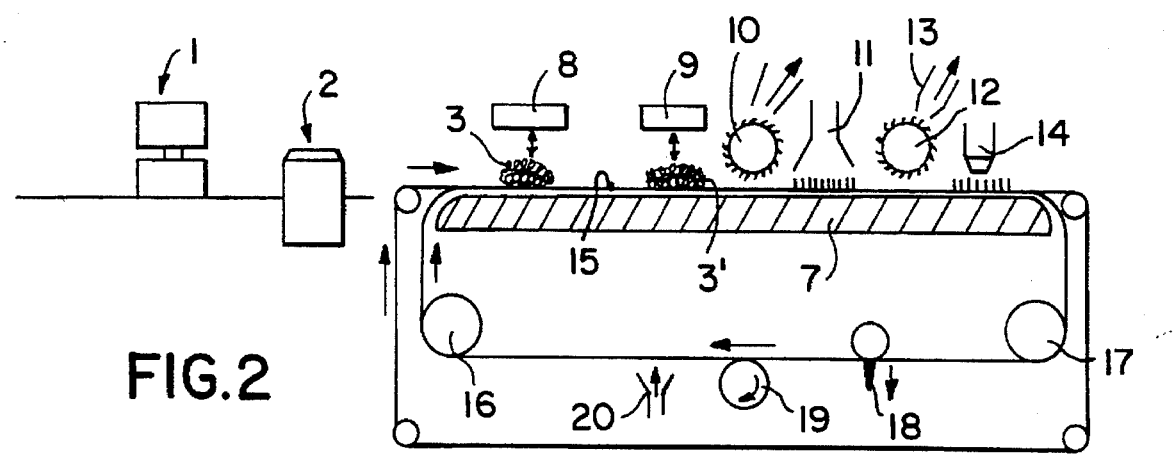
FIG. 2 shows in a similar way to FIG. 1 a variant of this method.

Thus, in the embodiment illustrated in FIG. 2 and in which the same reference numbers indicate similar elements which occur in both embodiments and which will not be described again, the aluminium sheet 4 has been replaced by a continuous metal belt 15, for example made of aluminium of suitable thickness and which circulates continuously by being driven under tension between the two rollers 16, 17, at least one of which is motor-driven.

The belt 15, at the exit from the station 14, is cleared as indicated at 18, for example by a scraper, of most of the materials which adhere to it, after which it is suitably cleaned by a roller or a brush 19 possibly impregnated with a solvent, and then dried at 20 before being re-used at the starting station 8.

Figure 3:
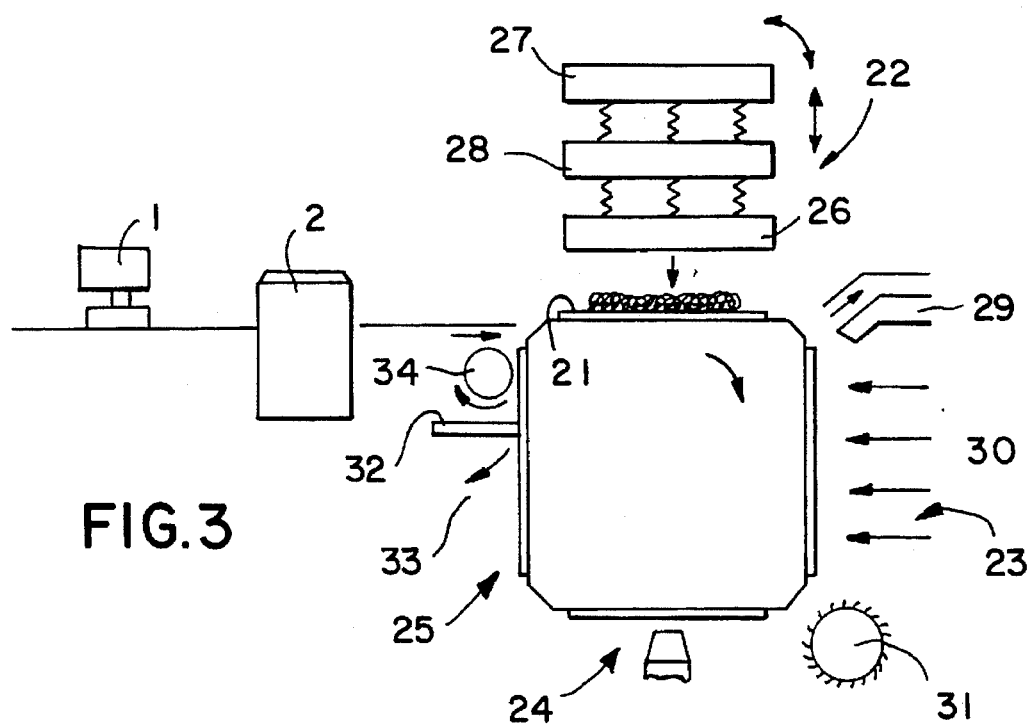
FIG. 3 is a diagram relating to a third variant.

In the variant illustrated in FIG. 3, instead of a metal belt which moves under the various successive stations, there are individual plates moving successively under the stations: 22 for application of the honey-dew onto the plate 21; 23 for the cleaning/heating of the sample in order to clear it of fibres; 24 for counting the honey-dew spots; and 25 for cleaning before re-use at station 22.

The station 22 may comprise a plate for hot pressing 26 and a plate for cold pressing 27 which are brought successively into action (after turning the whole system through 180°) and which are separated by an insulator 28.

The cleaning/fibre-removing station may comprise a suction/brushing zone 29 and a drying zone 30 as well as a brush 31 to remove the last fibres.

The cleaning station 25 may comprise a scraper 32 with removal of waste at 33 and a cleaning/drying brush 34.

Of course, it is possible to imagine many variants of the embodiments described schematically solely for the purposes of illustration. In particular, it is of course possible to work on larger or smaller samples, the important feature being to keep to a proportion in which the weight of the sample used is still small in relation to its surface area, i.e. preferably of the order of 2 to 5 g for 200 cm² in the examples given, a satisfactory range being for example from 0.5 to 5 g for 100 cm².

From the above description, it is to be understood that the method and the installation for evaluation in conformity with the invention may be completely automated and that the parameters acquired by this installation may be used to control in an appropriate manner any installation for treatment provided downstream.

In particular, an installation of the type described above may be used to control an installation for removal of honey-dews, especially by dissolving/modification using heated steam, by adapting the degree of treatment to the degree of contamination of the cotton.

I claim:

1. A method of evaluating the sticking characteristic of fibrous plant materials, the method comprising the steps of:
   a) preparing a sample of fibrous plant material having a relatively large surface area in relation to the weight of the sample;
   b) placing the sample on a metal support surface and, at a first pressing station, applying heat and pressure directly to the sample for a first selected period of time by pressing a heated pressing unit directly against the sample;

c) after the first selected period of time has elapsed, removing the heated pressing unit from the sample and advancing the sample, while supported on the support surface, from the first pressing station to a second pressing station;

d) at the second pressing station, cooling the sample under pressure on the metal support surface for a second selected period of time by pressing a cold pressing unit directly against the sample;

e) after the second selected period of time has elapsed, removing the cold pressing unit from the sample;

f) removing substantially all of the fibers of the sample from the metal support surface; and g) examining the metal support surface to evaluate the sticking characteristic of the fibrous plant material.

2. A method according to claim 1, further comprising the step of drying the sample with heated air, the drying step being performed after the step of cooling the sample under pressure.

3. A method according to claim 1, wherein the fibrous plant material is cotton.

4. A method according to claim 3, wherein the sample has a mass ranging from about 2 g to about 5 g and a surface area of about 200 cm$^2$.

5. A method according to claim 1, wherein the sample is heated under pressure at a temperature ranging from about 33° C. to about 140° C.

6. A method according to claim 4, wherein the sample is heated under pressure at a temperature ranging from about 33° C. to about 140° C.

7. A method according to claim 1, wherein the sample is heated under pressure at a temperature ranging from about 50° C. to about 90° C.

8. A method according to claim 6, wherein the sample is heated under pressure at a temperature ranging from about 50° C. to about 90° C.

9. A method according to claim 1, wherein the first selected period of time ranges from about 5 seconds to about 30 seconds.

10. A method according to claim 7, wherein the first selected period of time ranges from about 5 seconds to about 30 seconds.

11. A method according to claim 1, wherein the sample is heated under a pressure which is greater than 40 g (force)/cm$^2$.

12. A method according to claim 11, wherein the sample is heated under a pressure ranging from about 80 g(force)/cm$^2$ to about 500 g(force)/cm$^2$.

13. A method according to claim 7, wherein the sample is heated under a pressure ranging from about 80 g(force)/cm$^2$ to about 500 g(force)/cm$^2$.

14. A method according to claim 1, wherein the second selected period of time ranges from about 15 seconds to about 30 seconds.

15. A method according to claim 7, wherein the second selected period of time ranges from about 15 seconds to about 30 seconds.

16. An apparatus for evaluating the sticking characteristic of fibrous plant materials, the apparatus comprising:

a) means for preparing a sample of a fibrous plant material having a relatively large surface area in relation to its weight;

b) a metal support surface which receives the sample;

c) a heated pressing unit at a first pressing station, said heated pressing unit applying heat and pressure directly to the sample on the metal support surface;

d) means for removing the heated pressing unit from the sample and means for advancing the sample, while supported on the metal support surface, from the first pressing station to a second pressing station;

e) a cold pressing unit at a second pressing station, said cold pressing unit cooling the heated sample under pressure on the metal support surface;

f) means for removing substantially all of the fibers of the sample from the metal support surface; and g) means used to examine the metal support surface to evaluate the sticking characteristic of the fibrous plant material.

17. An apparatus according to claim 16, wherein the metal support surface comprises a continuous aluminum sheet extending from a feed roller to a take-up roller.

18. An apparatus according to claim 16, wherein the metal support surface is an endless belt.

19. An apparatus according to claim 18, wherein the endless belt is aluminum.

20. An apparatus according to claim 16, wherein the metal support surface is circuitous whereby the sample is successively positioned adjacent the heated pressing unit, the cold pressing unit, the means for removing substantially all of the fibers of the sample, and the means for examining the metal support surface to evaluate the sticking characteristic of the sample.

21. An apparatus for evaluating the sticking characteristics of fibrous plant materials, the apparatus comprising:

a) a system for preparing a sample of a fibrous plant material having a relatively large surface area in relation to its weight;

b) a metal support surface for receiving the sample;

c) a heating plate for applying heat and pressure to the sample on the metal support surface;

d) a cooling plate for removing heat and applying pressure to the sample on the metal support surface;

e) a device for removing substantially all of the fibers of the sample from the metal support surface; and f) a device used to read the number of spots left by the sample on the metal support surface.

22. The apparatus of claim 21, wherein said device for counting facilitates manual counting of the number of spots.

23. The apparatus of claim 21, wherein said device for counting automatically counts the number of spots.

* * * * *